United States Patent [19]
Fournier et al.

[11] Patent Number: 6,011,563
[45] Date of Patent: *Jan. 4, 2000

[54] COMPUTER CONTROLLED PHOTOIRRADIATION DURING PHOTODYNAMIC THERAPY

[75] Inventors: Ronald L. Fournier; Jeffrey Henning, both of Sylvania; James A. Hampton, Waterville; Steven H. Selman, Toledo, all of Ohio

[73] Assignee: The University of Toledo, Toledo, Ohio

[*] Notice: This patent is subject to a terminal disclaimer.

[21] Appl. No.: 08/427,668

[22] Filed: Apr. 24, 1995

[51] Int. Cl.[7] .............................. G06F 9/455; A61B 1/00; A61B 17/36
[52] U.S. Cl. ...................... 345/500; 128/653.1; 128/633; 378/65; 378/151; 606/2
[58] Field of Search .................................. 606/2; 395/500, 395/572; 128/633, 665, 630, 655, 653.1; 364/578; 607/88, 89, 90; 602/2

[56] References Cited

U.S. PATENT DOCUMENTS

| | | | |
|---|---|---|---|
| 3,783,251 | 1/1974 | Pavkovich et al. | 600/1 |
| 3,987,281 | 10/1976 | Hodes | 128/653.1 |
| 4,122,853 | 10/1978 | Smith | 128/303 |
| 4,336,809 | 6/1982 | Clark | 128/665 |
| 4,576,173 | 3/1986 | Parker et al. | 128/633 |
| 4,592,361 | 6/1986 | Parker et al. | 128/633 |
| 4,612,938 | 9/1986 | Clark | 128/665 |
| 4,630,273 | 12/1986 | Inoue et al. | 372/9 |
| 4,633,872 | 1/1987 | Chaffee et al. | 128/303 |
| 4,641,650 | 2/1987 | Mok | 128/303 |
| 4,672,963 | 6/1987 | Barken | 128/303 |
| 4,692,924 | 9/1987 | Koizumi et al. | 372/30 |
| 4,822,335 | 4/1989 | Kawai et al. | 604/20 |
| 4,862,888 | 9/1989 | Yessik | 128/303 |
| 4,994,059 | 2/1991 | Kosa et al. | 606/12 |
| 5,035,693 | 7/1991 | Kratzer et al. | 606/12 |

(List continued on next page.)

OTHER PUBLICATIONS

Marcus, Struart, Photodynamic Therapy of Human Cancer, pp. 869–889 IEEE, Jun. 1992.

Foster et al, Oxygen Consumption and Diffusion Effects in Photodynamic Therapy, pp. 296–301, IEEE, Jul. 1991.

De Jong et al, Microsoft Press, Computer Dictionary, pp. 361–362 Jan. 1994.

Foster et al, Oxygen Consumption and Diffusion Effects in Photodynamic Therapy Radiation Research, Jul. (1991).

Oxygen Comsumption and Diffusion Effects in Photodynamic Therapy, Thomas H. Foster, Richard S. Murant, etc., Radiation Research 126. 296–303 (1991), Jul. 1991.

*Primary Examiner*—Kevin J. Teska
*Assistant Examiner*—Herbert McNair
*Attorney, Agent, or Firm*—Brinks Hofer Gilson & Lione

[57] ABSTRACT

A system and method is provided for optimizing a laser light fractionation during photodynamic therapy of a tumor. The tumor is destroyed through the production of singlet oxygen and successful photodynamic therapy treatment requires the maintenance of tumor oxygen above a specified critical level. Depending on the tumor, the photosensitizer concentration, and the laser fluence, sustained irradiation of the tumor will deplete the oxygen below the critical level. When the laser is turned off, oxygen diffuses into the tumor to provide sustained levels of singlet oxygen. The control system controls the operation cycle of the laser and the various surgical parameters. Data regarding the sensitizer, the laser characteristics, and the oxygen features of the tumor are input into the control system for simulation of the PDT treatment. As part of the simulation, the optimal fractionation cycle for the laser is predicted. The data may be adjusted for conducting additional simulations. The simulation data and results are stored in the control system for controlling the actual PDT treatment cycle. A computer is linked to the laser and a beam splitter or other cycling device to control the fractionated photodynamic therapy irradiation process for optimal treatment of a specific tumor.

13 Claims, 6 Drawing Sheets

U.S. PATENT DOCUMENTS

| | | | |
|---|---|---|---|
| 5,049,147 | 9/1991 | Danon | 606/10 |
| 5,050,597 | 9/1991 | Daikuzono | 128/395 |
| 5,066,274 | 11/1991 | Bommer et al. | 604/20 |
| 5,098,427 | 3/1992 | Hessel et al. | 606/11 |
| 5,123,902 | 6/1992 | Müller et al. | 604/21 |
| 5,132,101 | 7/1992 | Vogel et al. | 424/9 |
| 5,140,984 | 8/1992 | Dew et al. | 128/395 |
| 5,150,704 | 9/1992 | Tatebayashi et al. | 128/395 |
| 5,154,707 | 10/1992 | Rink et al. | 606/12 |
| 5,291,404 | 3/1994 | Kurokawa et al. | 600/413.26 |
| 5,339,812 | 8/1994 | Hardy et al. | 128/653.1 |
| 5,391,081 | 2/1995 | Lampotang et al. | 434/262 |
| 5,438,991 | 8/1995 | Yu et al. | 128/653.1 |
| 5,458,125 | 10/1995 | Schweikard | 128/653.1 |
| 5,596,653 | 1/1997 | Kurokawa et al. | 382/128 |

COMPUTER CONTROLLED PHOTOIRRADIATION DURING PHOTODYNAMIC THERAPY

BACKGROUND OF THE INVENTION

1. Field of the Invention

The present invention relates to a computerized laser controller for photodynamic therapy ("PDT") treatment of various types of cancerous tumors, and in particular, to a system for optimizing the effect of the photodynamic therapy in treating the cancer by cycling the laser operation to ensure that the proper levels of singlet oxygen is present in the tumor. A medicated tumor is irradiated by a laser with a specific wavelength such that the cancerous tumor is destroyed with only minimal damage to the healthy tissue surrounding the tumor. Anoxia induced within the tumor is minimized to improve the therapeutic effectiveness of the PDT process.

2. Summary of Related Art

Cancer research has resulted in a number of important developments in the diagnosis and treatment of cancer. Although significant improvements have been developed for surgery, radiotherapy, chemotherapy, and related treatments, all such treatments are associated with major debilitating side effects. The side effects, such as trauma, immunosuppression, or toxicity, present further obstacles to the patient in ill-health.

One of the newer treatment methods which has been developed for intractable tumor masses is photodynamic therapy. Photodynamic therapy offers a viable, less toxic, less invasive, and less painful procedure for treatment of cancer. Solid tumors, frequently characterized by a poorly developed vascular system and sometimes inoperable, are good candidates for photodynamic therapy.

Photodynamic therapy generally involves the infusion of photoactivatable dyes, followed by appropriate long wavelength irradiation of the tumors to generate a lethal short-lived species of oxygen which destroy the neoplastic cells. Early photodynamic therapy agents were derived from natural sources or from known chemicals originating in the dye-stuffs industry.

Improved chemically pure photoactivatable dyes have been chemically synthesized for use in photodynamic therapy. The dyes used in photodynamic therapy are compounds with low intrinsic toxicity, are efficient photosensitizers for singlet oxygen production, have selective uptake in rapidly proliferating cells, are rapidly degraded and eliminated from the tissues after administration, and are available as chemically pure and stable compounds easily subject to synthetic modification.

The latest photodynamic therapy dye compounds exhibit a maximum wavelength absorption at between about 600 to 900 nm. The longer wavelength absorption characteristics facilitates the use of such compounds as photodynamic therapy agents while minimizing the competing light absorption by blood and other tissues which absorb in the shorter wavelength regions below 600 nm.

The photodynamic therapy agents are prepared in a pharmaceutical composition or preparation for either topical and parenteral applications. After administration of a therapeutically effective amount of the agent to a patient having a treatable condition, such as a solid tumor, the patient's affected body area is exposed to a sufficient amount of light having an appropriated wavelength for absorption by the particular photodynamic therapy agent used. Irradiation of the accumulated agent generates singlet oxygen which is thought to be the actual lethal species responsible for destruction of the neoplastic cell.

Photodynamic therapy agents, in general, are minimally toxic in the unexcited state. The agents can be repeatedly photoactivated and lead each time to cell-lethal events, by the generation of singlet molecular oxygen. The half-life of singlet molecular oxygen is measured in microseconds, and the target cell is affected without the opportunity for migration of the lethal singlet molecular oxygen to healthy neighboring tissue. Destruction of the target cell tissue commences promptly upon irradiation of the agent, and ceases abruptly when irradiation is stopped.

The time and duration of therapy can be selected by the physician or radiologist. The dosage of photodynamic therapy agent may be varied according to the size and location of the target tissues which are to be destroyed and the method of administration. Irradiation generally takes place not less than one hour or more than four days after parenteral administration of the agent. With topical agents, irradiation may commence as soon as 10 minutes after application.

The oxygen tension of tumors treated with ionizing radiation is an important factor influencing radiosensitivity and therapeutic response. Treatment under hyperbaric oxygen conditions and fractionation of the light dosage are two methods for exploiting the increased sensitivity of well-oxygenated tumors.

Tumor destruction in photodynamic therapy is accomplished through the formation of singlet oxygen, and the subsequent reaction of singlet oxygen with cellular substrates. Considerable attention has been given to the calculation and measurement of the sensitizing agent and the light dose delivered to a tumor undergoing photodynamic therapy. While sufficient quantities of light and photodynamic therapy agent are prerequisites for the photodynamic effect, it is clear that the production of cytotoxic levels of singlet oxygen depends directly upon the presence of ground state molecular oxygen as well.

Photodynamic therapy is dependent on the presence of molecular oxygen in the tumor tissue. Tumor response to the same light and agent dose varies significantly with the rate of light delivery to the neoplastic cell. Oxygen depletion at high dose rates may contribute to diminished tumor cell killing. Photodynamic therapy is capable of consuming oxygen at a rate that is sufficiently high to move a fraction of the treated tumor volume into very low oxygenation, thereby protecting these cells from damage mediated by singlet oxygen.

The intercapillary tissue can become hypoxic shortly after treatment begins. Anoxia induced by PDT outside a critical radius from the capillaries can serve to inhibit direct tumor cell destruction. The cells immediately surrounding the capillaries, to which oxygen may diffuse from the microvasculature, are directly affected by the PDT reaction. Fractionating the exposure to light may enhance the efficacy of the PDT treatment. Cycling the photoirradiation creates dark intervals which halt the mechanisms of the PDT reaction and allow time for oxygen to diffuse back into the anoxic intercapillary spaces, resulting in periodic production of and exposure to the toxic effects of singlet oxygen.

Photodynamic therapy has been used both experimentally and clinically for treatment of cancer tumors. Fractionating has improved the results of photodynamic therapy by overcoming oxygen depletion. However, a system to optimize the fractionation of the light dose through laser control is needed to improve the clinical applications of photodynamic therapy.

A number of researchers have discussed the concept of fractionating the light source to improve oxygenation and the therapeutic response of PDT. (Foster et al., Analysis of Photochemical Oxygen Consumption Effects in Photodynamic therapy in Optical Methods for Tumor Treatment and Detection: Mechanisms and Techniques for Photodynamic Therapy, *SPIE*, 1645:104–114 (1992); Foster et al., Oxygen Consumption and Diffusion Effects in Photodynamic Therapy, *Radiation Research*, 126: 296–303 (1991); Foster and Gao, Dosimetry in Photodynamic Therapy: Oxygen and the Critical Importance of Capillary Density, *Radiation Research*, 130: 379–383 (1992); and Gibson et al., Effects of Various Photoradiation Regimens on the Antitumor Efficacy of Photodynamic Therapy for R3230AC Mammary Carcinomas, *Cancer Research*, 50: 7236–7241 (1990)). The general improvements achieved by fractionating of the light source have been considered from an experimental standpoint.

One of the factors which increases the cost of photodynamic therapy treatment is the clinical time needed for operating a laser system for treating a cancerous tumor. Doctors, radiologists, and technical staff must carefully operate a complex laser system to concentrate the laser beam on the tumor. Cancer clinics have a need for a system to improve the efficiency of the photodynamic therapy by decreasing the time needed for laser treatment.

Laser systems have been used in various surgical procedures for a number of years. Inoue et al. (U.S. Pat. No. 4,630,273) shows a laser system with a programmable memory system for storing a variety of irradiating modes.

Barken (U.S. Pat. No. 4,672,963) teaches a system and method for computer controlled laser surgery. An ultrasonic probe is used to monitor the condition of the tissue and the position of the laser irradiating device. The computer system provides image reconstruction and monitors the systems parameters such as laser power. The computer controls the laser power and on/off cycle times.

The device for the selective destruction of cells disclosed by Kratzer et al. (U.S. Pat. No. 5,035,693) includes an X-Y optical scanning device. The process involves an initial low power illumination step, a response from the cells, detection by a control means, and a transmission of a high power radiation signal to kill the cells. The goal of such a system, is to provide accurate treatment of a large number of cells.

Danon (U.S. Pat. No. 5,049,147) teaches an apparatus for displaying in real time a visually sensible image of the area of surgery and an overlap of a simulation of the effects of operator indicated laser surgical procedures. Once the laser system is properly positioned and aligned, the high energy is fired to carry out the indicated laser surgical procedure from the display.

SUMMARY OF THE INVENTION

In accordance with the present invention, there is provided a interactive laser control system for controlling a laser light beam during photodynamic therapy. The tumor is destroyed through the production of singlet oxygen and successful photodynamic therapy treatment requires the maintenance of tumor oxygen above a specified critical level. Depending on the tumor, the photosensitizer concentration, and the laser fluence, sustained irradiation of the tumor will deplete the oxygen below the critical level. When the laser is turned off, the oxygen diffuses into the tumor to provide sustained levels of singlet oxygen.

The present invention includes a control system to control the operation cycle of the laser and the various surgical parameters. Data regarding the sensitizer, the laser characteristics, and the oxygen features of the tumor are input into the control system for simulation of the PDT treatment. As part of the simulation, the optimal fractionation cycle for the laser is predicted. The data may be adjusted for conducting additional simulations. The simulation data and results are stored in the control system for controlling the actual PDT treatment cycle. A computer is linked to the laser and a beam splitter or other cycling device to control the fractionated photodynamic therapy irradiation process for optimal treatment of a specific tumor.

A one-dimensional transient model of oxygen levels has been developed to accurately predict the oxygen levels surrounding a capillary in the tumor. The system analyzes the transient behavior to determine the optimal fractionation of the laser light dose based on a simulated treatment process. The results of the simulation are stored for use in controlling the actual PDT treatment process. The control system automatically adjusts the power setting of the laser and the cycle time for the fractionation of the laser.

In one embodiment, a beam splitter is placed between the laser and the patient to achieve the desired cycle. Instead of turning the laser on and off for each cycle of the treatment, the desired power setting and positioning of the laser is maintained while the beam splitter is controlled to alternatively direct the laser beams at the patient and then away from the patient.

In the control system, the physical parameters, reaction rates, diffusivities, and boundary conditions are entered into the computer of the control system. Maximum and minimum oxygen levels are observed during a simulated treatment process to determine the on and off cycle for the laser. During the simulation process, adjustments to the fractionating cycle can be observed. The computer processes and store the information for the simulations. During the actual treatment, the desired treatment process is recalled and used to control the laser and the beam splitter.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Photodynamic therapy (PDT) involves localized photoirradiation of dye-sensitized tissue of a tumor in order to kill the cells of the tumor. After a sensitizer is introduced to the tissue of a tumor, the affected tumor is irradiated with light of proper wave length (600 to 900 nm) to generate excited singlet oxygen molecules of the sensitizer.

Figure 1:
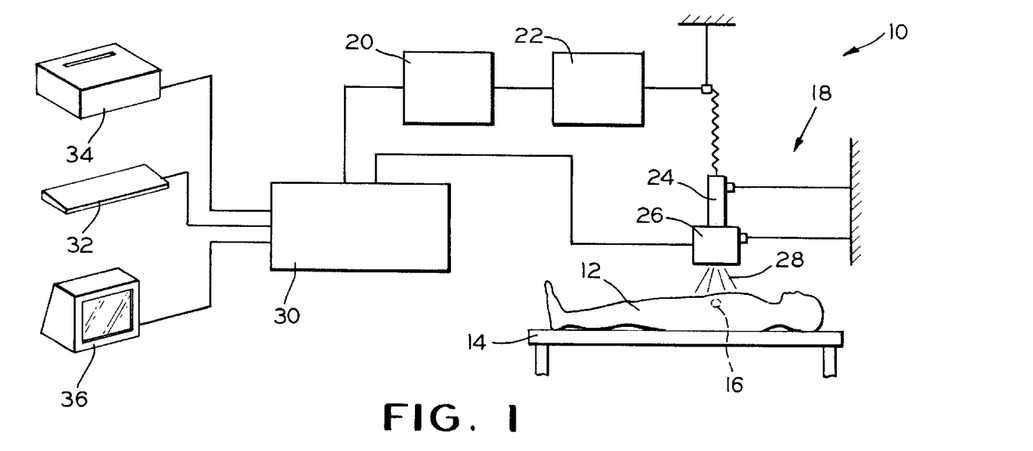
FIG. 1 is a general layout of the PDT system with computerized control system.

Referring now to FIG. 1, a diagram of laser system 10 for the present invention is shown. A patient 12 is placed on a table 14 for treatment of a tumor 16 in which a sensitizer has been introduced. A positioning means 18 is used to position the beam splitter (shutter) and the laser light conduit/guide over the patient 12. The power supply 20 and laser unit 22 are connected to the light conduit 24 for generating the necessary laser light beam.

In the PDT treatment process, the laser light beam 28 is directed at the desired spot on the patient in a controlled on-off cycle to optimize the efficiency of the process. Fiber optics may be used to optically guide the beam into the body.

The fractionation of the laser light beam can be achieved in several different methods. The on-off (light-dark) cycle could be achieved by directly turning the laser light beam on and off. The laser light system has a ramp-up time to reach the specified power rating. In fractionation cycles with short cycles, the ramp-up time could effect the results of the irradiation. In addition, the continuous on and off cycle would place undue wear and tear on the laser system 10 and is more difficult to control. Consequently, a beam splitter 26 or other shutter device may be used to direct the laser beam 28 towards the patient 12 for a specified light time and then direct the laser beam 28 away from the patient 12 for the of dark time of a cycle.

A computer 30 is used to monitor the condition of the tumor 16 and to control the operation cycle of the laser unit 22, light conduit 24, and beam splitter 26. A keyboard 32 is connected to the computer 30 for inputting data and control information. A printer 34 and monitor 36 are used to monitor and observe the results of the treatment.

The computer 30 is used to conduct one or more simulations of a PDT treatment process based on the data inputted into the computer 30. The optimum fractionation cycle is determined as part of the simulation process. The data and results of the simulations are stored in the computer 30 for use during the actual PDT treatment process. The desired simulation is specified in the control system 10 and the computer 30 controls the laser unit 22 and beam splitter 26 during the PDT treatment process. After the actual PDT treatment, the results of the treatment are reviewed and correlated to the results predicted by the simulation.

During photodynamic therapy at the time of the irradiation of the sensitizer in the tumor 16, the singlet molecules of the sensitizer may either decay back to the ground state (fluorescence) or may alternatively transform to a triplet sensitizer state. The triplet state has only a slightly lower energy level than the excited singlet state.

A reaction occurs which results in lipid peroxidation to kill the cells of the tumor. Energy is transferred from the triplet sensitizer to molecular oxygen. Molecular oxygen is generally referred to as the triplet or ground state oxygen, and upon receipt of the energy transfer, singlet oxygen is the excited electron state of ground state oxygen. The singlet oxygen formed by the energy transfer oxidizes the lipid structure through the action of the singlet oxygen.

The cell destruction in the tumor is caused by the lipid peroxidation by the singlet oxygen. The singlet oxygen is generated by the transfer of energy from the laser system to the triplet sensitizer to the ground state oxygen. The presence of ground state oxygen is required in order to generate additional singlet oxygen.

Some tumors maintain large avascular regions that are anoxic even under normal metabolism and will resist PDT treatment under all situations. Other tumors are so densely populated with capillaries that even under the added oxygen consumption of PDT irradiation, the intercapillary tissue is well oxygenated and proves extremely responsive to PDT.

Other tumors are vascularized in such a way that under normal metabolic oxygen consumption, the oxygen levels in the intercapillary regions are always positive. However, under PDT radiation, the reaction mechanism to create the singlet oxygen consumes the ground state oxygen at such a rate that the oxygen is maintained only within a critical radius about the capillaries. Cells outside of the critical radius are effectively insulated from the direct toxic effects of the treatment and resume normal cell function as soon as treatment ends and oxygen diffuses back into the areas. Thus, once the oxygen is depleted in the areas outside of the critical radius, only the tissue cells immediately surrounding the capillaries, to which oxygen may diffuse from the blood stream in the capillaries, are directly affected by a continuous PDT reaction process.

The intercapillary tissue can become hypoxic in as little as thirty seconds after commencement of the PDT irradiation. While the regions between the capillaries are protected due to lack of oxygen, the areas within the critical oxygen diffusion distance are still under attack by the PDT process. This brings about vascular occlusion without rendering much damage to cells outside the oxygen diffusion distance.

Figure 2:
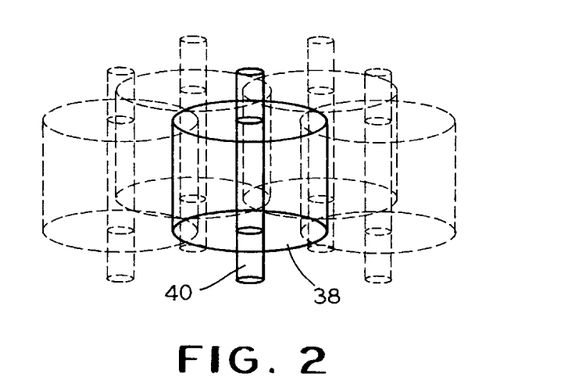
FIG. 2 shows a three dimensional depiction of a capillary and surrounding tissue.

Due to the extremely small physical scale on which PDT reactions occur, direct or indirect measurements of control parameters in the PDT process is difficult. Consequently, mathematical modeling is used to simulate the actual process and to develop control signals for an actual PDT treatment. The Krogh tissue model may be used to determine capillary diffusion processes. As shown in FIG. 2, a single capillary 40 and its surrounding tissue 38 are considered a cylinder with the capillary 40 forming a center longitudinal axis. The radius of the tissue cylinder 38 is considered to be half the average distance separating any two capillaries in the tissue. oxygen levels are dependent upon the intercapillary spacing within the tumor and the laser fluence rates during PDT therapy.

In order to optimize the PDT process, the creation of anoxic regions in the tumor should be avoided. The direct PDT process would be enhanced by allowing the vasculature to undergo direct cell killing at no greater rate than the most distant intercapillary tumor cells. The true optimization of the PDT process requires the scheduling of light intervals so as to maintain a minimum oxygen level within the tissue.

Figure 3:
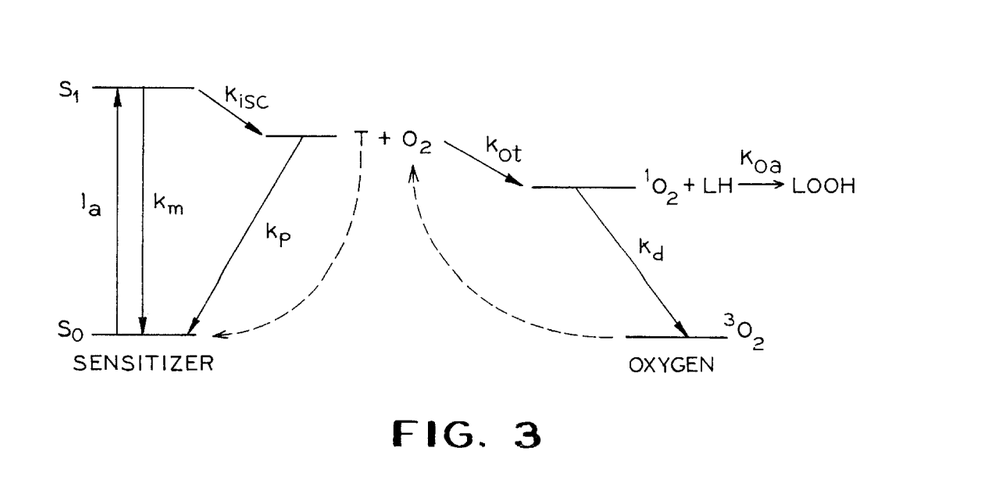
FIG. 3 depicts an energy diagram showing the species transitions.

The photochemical process in the PDT process is shown in the energy diagram in FIG. 3. The sensitizer excitation rate ($I_a$) is a function of the irradiance, tissue penetration depth, sensitizer properties, and sensitizer concentration. In addition to the singlet oxygen decaying back to ground state, the singlet oxygen may also react with the cellular substrate, A, at a rate of $k_{oa}$. The following set of equations describes the rate of species consumption per unit tissue volume based on the above PDT process:

$$R_{S1} = I_a - k_m c_{S1} - k_{isc} c_{S1}$$

$$R_T = k_{isc} c_{S1} - k_{ot} c_{3O2} c_T - K_p c_T$$

$$R_{3O2} = -S_\Delta k_{ot} c_{3O2} c_T + K_d c_{1O2}$$

$$R_{1O2} = S_\Delta k_{ot} c_{3O2} c_T - k_d c_{1O2} - k_{oa} c_{1O2} c_A$$

$$R_A = -k_{oa} c_{1O2} c_A$$

where $R_i$=the reaction rate of species i ($\mu$M/s)

$C_i$=the local concentration of species i ($\mu$M)

$I_a$=the singlet sensitizer excitation rate as determined by the laser fluence ($\mu$M/s)

$k_m$=the direct decay rate of singlet sensitizer to ground state ($s^{-1}$)

$k_{isc}$=the decay rate of singlet sensitizer to the triplet state ($s^{-1}$)

$k_p$=the decay rate of triplet sensitizer to the ground state ($s^{-1}$)

$k_{ot}$=the second order rate at which triplet sensitizer imparts its energy to ground state oxygen thus creating the singlet oxygen state ($\mu M^{-1}-s^{-1}$)

$S_\Delta$=the percentage of T-$3O_2$ collisions that lead to the formation of singlet oxygen $k_d$=the decay rate of singlet oxygen back to ground state ($s^{-1}$)

$k_{oa}$=the reaction rate of singlet oxygen with the cellular substrate ($\mu M^{-1}-s^{-1}$)

A term that needs to be calculated is the $I_a$ value which depends on the laser fluence rate ($\Phi_0$) incident on the tissue and the tissue depth, x, at which $I_a$ is being measured. The equation for determining $I_a$ is:

$$I_a = 2303(\Phi_0 \lambda_e C/hcN_a)10^{\epsilon \backslash Cx} (M/s)$$

where $\Phi_0$=Laser fluence rate (W/cm$^2$)

$\lambda$=Light wavelength (m)

$\epsilon$=Sensitizer extinction coefficient ($M^{-1}$ cm$^{-1}$)

C=Sensitizer concentration (M)

h=Plank's constant (6.626×10$^{-34}$ J-s)

c=speed of light (m/s)

$N_a$=Avogadro's number (6.023×10$^{23}$ mole$^{-1}$)

x=sample thickness (cm)

A transient model of the PDT process requires the continuity equation for each species, i. These equations must be solved simultaneously. The general form of the continuity equation appears below.

$$\partial C_i/\partial t + (\nabla \cdot \backslash c_i V^*) = (\nabla \cdot cD_i \partial x_i) + R_i$$
(transient) (convection) (diffusion) (generation)

where $c_i$=species concentration v*=bulk velocity c=total molar density of the mixture D=diffusion rate of species through mixture $x_i$=mole fraction of species $R_i$=generation/consumption rate of species If the cellular substrate (A) is assumed to be stationary (v*=0) and very nearly steady state, this yields a set of four simultaneous partial differential equations. This equations set is very difficult to solve. However, two characteristics of the reaction mechanism allow us to make drastic simplifications to the equation set. First, the diffusion rates of all but ground state oxygen are very much slower than their reaction rates. Therefore, all species, except ground state oxygen, can be assumed not to diffuse. That is to say, the distances that these molecules diffuse through the tissue before they react is so small that they can be assumed to be stationary in the solution domain. This means that the diffusion terms for the singlet sensitizer, triplet sensitizer and singlet oxygen equations can be neglected. Second, the triplet oxygen reaction and diffusion rates are very much slower than the reaction rates of the other species. Therefore, all species may be considered to maintain a pseudo-steady-state equilibrium with the current local ground state oxygen concentration.

As a result of these two assumptions, the equation set may be reduced to a single partial differential equation describing the transient ground state oxygen behavior, and three simple algebraic equations which determine the local concentrations of the other species based on the ground state oxygen solution.

$$\frac{\partial c_{3O_2}}{\partial t} = \mathcal{D}_{3O_2} \nabla^2 c_{3O_2} \ldots - S_\Delta \phi_t I_a \left( \frac{1}{1 + k_d/k_{oa}c_A} \right) \cdot \left( \frac{1}{1 + k_p/k_{ot}c_{3O_2}} \right) \ldots - \Gamma$$

Boundary condition 1:
@ capillary wall, $c_{3O_2} = C_0$

Boundary condition 2:
@ symmetry plane, $\nabla^2 c_{3O_2} = 0$

Initial condition:
@ $t = 0$, $c_{3O_2} = C_0$ or metabolic profile $$c_S = \frac{I_a}{k_m + k_{isc}}$$

$$c_T = \phi_t \cdot \frac{I_a}{k_{ot} c_{3O_2} + k_p}$$

$$c_{1O_2} = \frac{S_\Delta \phi_t I_a}{k_d + k_{oa} c_A} \cdot \frac{1}{1 + \frac{k_p}{k_{ot} c_{3O_2}}}$$

The above non-linear, first-order partial differential equation lends itself well to solution using standard finite difference methods. Solution yields a prediction of the triplet oxygen concentration profile through a tissue slice or Krogh cylinder as it changes with time. The other species may then be determined from the predicted triplet oxygen concentrations in space and time.

The computer program for the control system of the present invention solves the partial differential equation that describes time dependent oxygen diffusion using the Thomas Algorithm for solution of tridiagonal matrices. Once the triplet oxygen profile is obtained, the three algebraic equations are used to determine the other species.

After the data has been input into computer 30 and the initial predictions of the variable species are determined, an optimum operating cycle for fractionating the laser beam 28 is used to generate control signals for controlling the operation of the beam splitter 26. Control measurements are monitored and the computer 30 generates a control signal for fractionation of the laser beam 28 from the beam splitter 26.

The initial control data which may be entered into the computer 30 for each photodynamic therapy treatment include the species diffusion rates, the reaction rates, the light intensity settings, sensitizer properties and the physical parameters of the photodynamic therapy analysis. Such data is initially entered at keyboard 32.

As noted in the above analysis, the only diffusion rate of any consequence to the photodynamic therapy is the oxygen diffusion rate. The reaction rate constants for a given sensitizer ($O_t$, $k_p$, $S_\nabla$, $k_o$, $k_d$, $k_{oa}$) and the metabolic oxygen consumption rate ($\Gamma$) are also entered into the computer 30 or may exist as a data base in the computer 30. The initial values may be updated as more accurate measurements of the rate constants are obtained.

The sensitizer activation rate ($I_a$) can be directly entered into the computer 30 or may be calculated by the computer from the light intensity and photochemistry parameters. Additional information regarding the sensitizer must also be entered into the system, such as the sensitizer extinction coefficient, molecular weight, and activation wavelength. Once these values for a specific sensitizer are entered, no further adjustments to such constants are typically required. The computer 30 may retain in memory the sensitizer data for repeated use of such sensitizer in subsequent photodynamic therapy.

The sensitizer concentration must also be entered into the computer 30. The typical concentration values range from 4 to 10 $\mu$gm/ml for the most common sensitizers.

The laser parameters must also be entered into the computer 30. The computer 30 is connected to the laser unit 22 such that the photoradiation intensity and laser wavelength may be set on the keyboard 32 or on the manual controls to the laser unit 22. The intensity and wavelength settings are monitored by the computer 30 for determining the fractionating cycle.

A light path length must be included for processing by the computer 30. The light is most intense just under the surface of the tumor. The setting used for the fractionation cycle is one-half of the thickness of the tumor.

The computer 30 is programmed for calculating and controlling the fractionation cycle. Flexibility has been included to provide analysis for both a Krogh tissue cylinder in-vivo analysis and a planar, one dimensional analysis that is more adaptable to laboratory experiments. If a Krogh cylinder analysis is elected, the capillary diameter and intercapillary distance must be entered into the computer 30. For a one dimensional analysis, the tissue thickness is the only input for the physical setting. The starting oxygen profile is also inputted into the computer 30.

Additional data which is entered into the computer 30 is the lower and upper limits for triplet oxygen. The lower limit is the minimum concentration of oxygen to be reached in the tissue 38 during irradiation of the tumor 16 during a light cycle of a PDT treatment process. The upper limit of the triplet oxygen represents the concentration of the oxygen in the tissue 38 during a dark cycle as the oxygen diffuses from the capillary 40 into the tissue 38.

After all the data is input into the computer 30, a simulation of the photodynamic therapy is conducted by the computer 30. The laser on/off cycle or fractionation may be controlled by preset time values, or by response to maximum and minimum oxygen levels at the symmetry plane between capillaries. The fractionation cycle is observed for a selected simulation time. The time for the actual treatment process may be controlled by a preset time value or by response to the fractionation cycle times.

During the simulation, the output of chemical species may be monitored on the display monitor 36. The results may be stored in the computer 30 or onto a disc for future use in controlling the beam splitter 26 during an actual therapy session.

A number of different outputs may be observed on the monitor 36 during the simulation. A profile view may be selected to provide an animation of the moving concentration profile between the capillary 40 and the symmetry plane as it changes with time. A centerline view is available to display a concentration versus time plot of the requested species at the symmetry plane between the capillaries. A flux plot displays the species flux rate at the capillary wall for ground state oxygen. The profile and centerline plots are generally available for the triplet sensitizer, the ground state oxygen, and the singlet oxygen species. The desired output for the simulation results is selected prior to the running of the simulation program.

After all of the parameters and output options have been selected, the simulation program is run by computer 30 based on the mathematical analysis noted above. The computer 30 generates a concurrent plot of the selected specie as the simulation progresses. The simulation is terminated once the simulation time limit has been reached or by manually terminating the simulation at the keyboard 32.

The results of the simulation may be stored in the computer 30 or a disc for future use and reference. The parameters can be varied to test a number of different options for treatment of a tumor. Different sensitizers can be tested without having to perform actual treatments. Different laser settings may be considered to determine the necessary treatment time and on-off cycles for fractionating the laser output.

Once an appropriate treatment for the photodynamic therapy is selected, the medical staff selects the data which has been stored during the simulation for actual operation of the PDT treatment. The computer 30 signals the laser unit 22 to control the laser beam 28 at the light conduit 24. The computer also signals the beam splitter 26 to control the on-off cycling of the laser beam 28 to the patient 12. The computer 30 receives control signals verifying the performance of the laser unit 22 and the beam splitter 28 to ensure that the desired treatment is being implemented.

The ability of the system 10 to simulate a variety of treatment options without knowing the exact tumor parameters is of major benefit in photodynamic therapy. A number of options can be tested by the simulation process, even if estimates of the reaction rates or capillary distances are not known. The actual photodynamic therapy process can be administered with a high degree of accuracy based on the computer control of the laser 22 and the beam splitter 26.

As the actual results of the photodynamic therapy on the patient are correlated with the simulated therapy process, the reaction rates and other parameters may be selected with greater accuracy for the various types and sizes of tumors. Consequently, the fractionated light delivery will be more effective and efficient in providing optimum photoradiation therapy.

Figure 4:
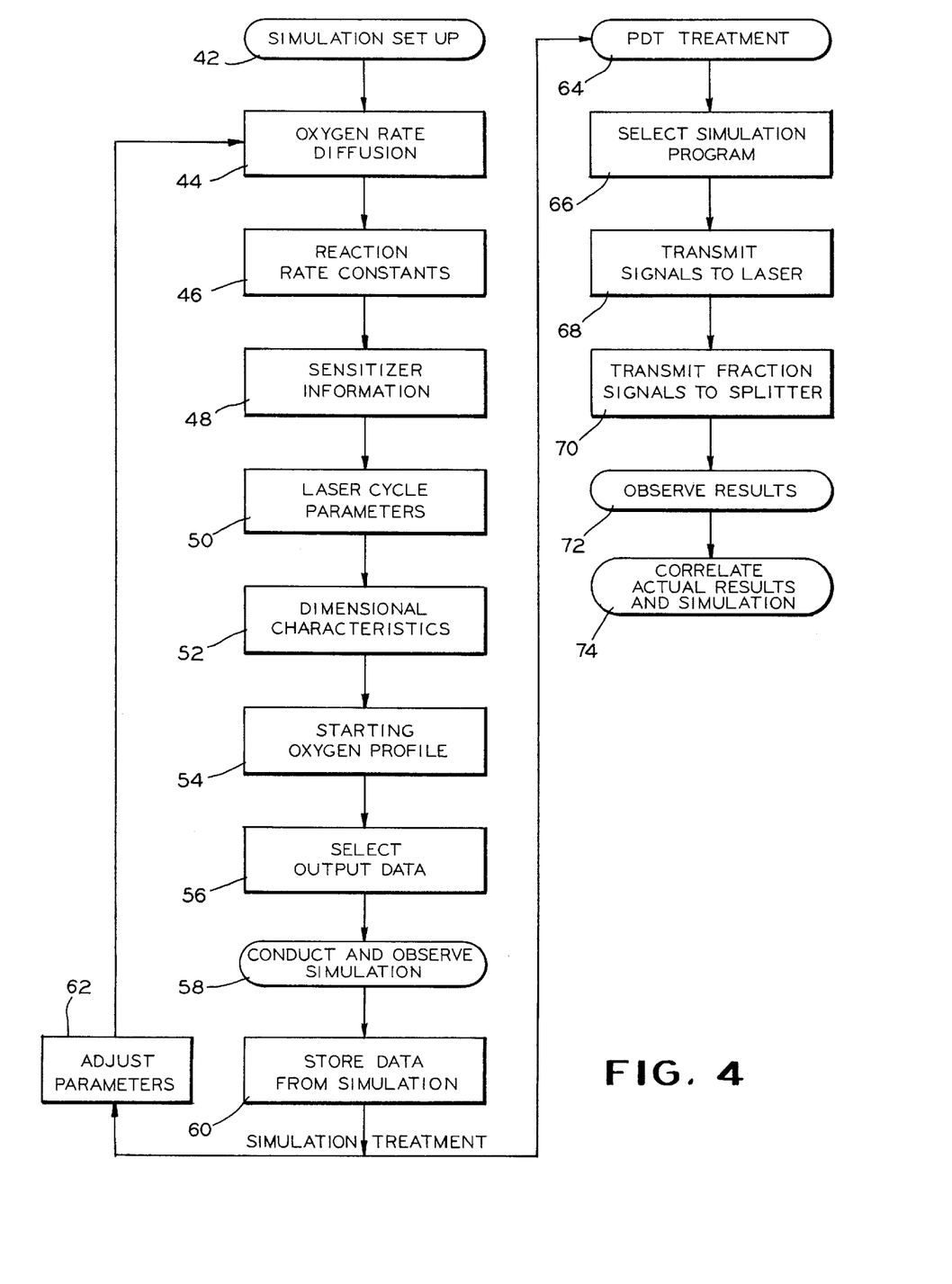
FIG. 4 is a diagram of the control parameters used to generate the preferred fractionation cycle for the laser.

The details for the simulation and control of the laser system 10 are shown in the flow chart of FIG. 4. The simulation setup 42 is the first step in the process. The specific data for the simulation is then entered into the computer 30 at keyboard 32. The oxygen rate diffusion 44, reaction rate constants 46, sensitizer information 48, laser cycle parameters 50, dimensional characteristics 52, and starting oxygen profile 54 are the factors to be inputted.

The next step in the process is to select the output data 56 for observation during the simulation process. This step includes inputting either specific fractionation time or the lower and upper limits for triplet oxygen. The total simulation time is set in seconds and is distinct from the setting of the total time for the actual treatment. The simulation does not need to be conducted for the full treatment time of the actual PDT treatment process, which is preset or calculated independent of the simulation time. Data from each simulation can be observed 58 and stored 60 on the computer 30 or on a computer disk.

Once the initial simulation is completed, the medical staff can either adjust the variables 62 and conduct another simulation, or save the stored data for use in the actual PDT treatment 64 of a patient 12. A number of simulations can be conducted in a timely and cost efficient manner.

When the patent 12 is ready for a PDT treatment 64, the optimum or preferred program is selected from the computer storage 66. The patent 12 is positioned for treatment and the computer generates the control signals to operate the laser 68 and the beam splitter 70. The results are monitored and observed with each patient 12. The actual results can be compared to the simulation process 74 so that the future simulations and PDT treatments will provide a more exact correlation. The use of the system 10 provides the patient 12 with more effective treatment and achieves significant efficiencies and cost savings on the use of the system 10.

The basic premise for fractionated light delivery is that in certain types of tumors, the capillaries 40 are sufficiently sparse causing hypoxia in the cells furthest from the capillaries 40 during PDT, but not under normal metabolism. These cells, being temporarily devoid of oxygen, are then insulated from the toxic effects of PDT. A critical radius is determined by the radius at which the oxygen from a given capillary 40 will fall to zero.

Figure 5:
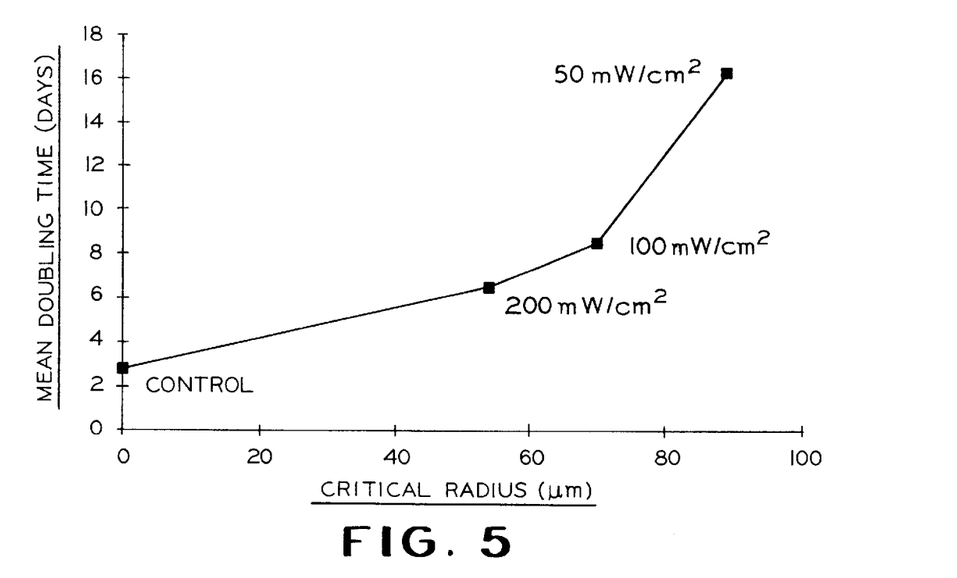
FIG. 5 is a graph showing the relationship at various fluence rates between the critical radius of cells around a capillary beyond which there is no longer any oxygen and the mean doubling times reported in the prior art.

FIG. 5 shows a comparison of the doubling time values obtained from the prior art (Foster et al.) with predicted critical radii for samples treated with continuous irradiation at several fluence rates. The oxygen diffusion coefficient was selected at $1.6 \times 10^{-5}$ $cm^2s^{-1}$ with capillary oxygen concentration of 63 $\mu M$ with a capillary radius of 5 $\mu m$. Under continuous fluence of 50, 100 and 200 $mW/cm^2$, the oxygen consumption rate is 8.6, 17, and 34 $\mu M/s$, respectively. The critical radii are calculated to be 89 $\mu m$, 70 $\mu m$ and 53 $\mu m$.

The steady state model indicates that the more cells 38 around the capillary 40 are exposed to oxygen, the better the direct killing effect of the PDT irradiation. The critical radius defines the limits of singlet oxygen in the tissue 38. The tissue immediately surrounding the capillary within the critical radius may be referred to as the steady state core volume (SVC).

The PDT system 10 of the present invention can be used to observe the time required to reach steady state in a continuous irradiation process. The parameters inputted into the system are based on the treatment of an R3230AC mammary adenocarcinoma with the sensitizer Photofrin II.

Figure 6:
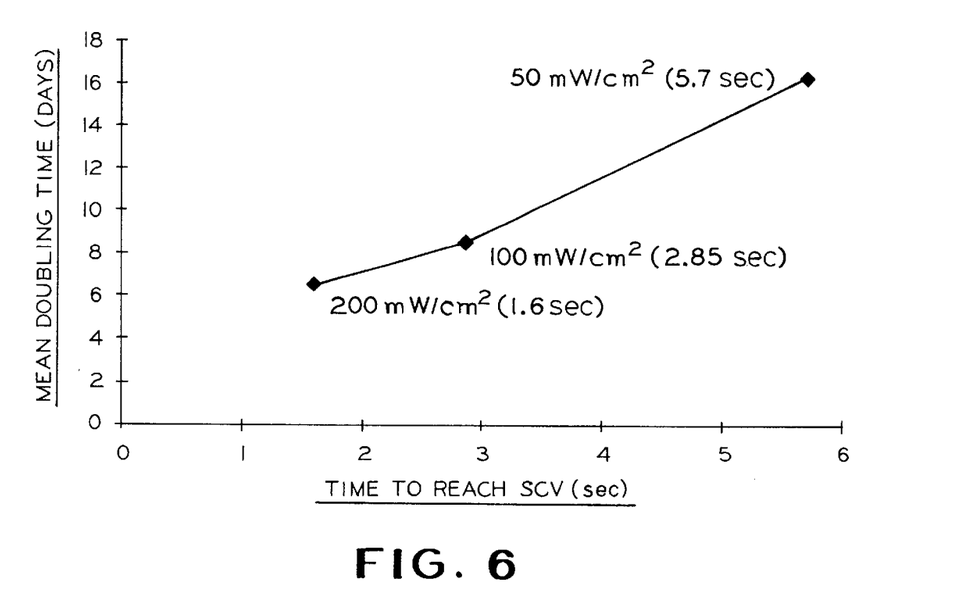
FIG. 6 is a graph showing the time required to reach the critical radius at various fluence rates and the mean doubling times.

FIG. 6 shows the comparison between the time to reach the steady state core volume and the mean doubling times as known in the prior art (Foster et al.). The longer it takes the oxygen to reach a steady state profile, the longer the cells outside the SVC are exposed. The positive correlation indicates that the duration of time that the cells outside the SVC are exposed to singlet oxygen is of equal or greater importance than the size of the SVC.

Fractionation cycles are used in an attempt to re-oxygenate the tissue 38 which is outside the steady state core volume. During the dark intervals, oxygen diffuses into the hypoxic regions under normal metabolic consumption rates.

Figure 7:
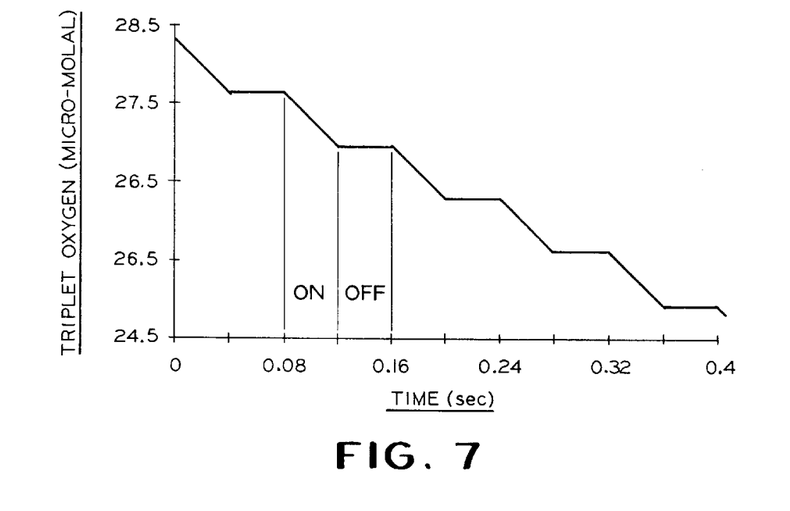
FIG. 7 is a graph showing the remote cell triplet oxygen during 40 ms fractionation of the laser.

FIG. 7 provides an overview of the transient nature of the effects of PDT by considering oxygen levels in remote cells, the cells furthest from a capillary wall. The analysis is for cells located half way between the average capillary separation distance. When the dark interval is too short, not enough time is provided to allow oxygen to diffuse in from the capillary. The oxygen concentration remains fixed during the dark intervals and continues to fall during the light intervals.

Figure 8:
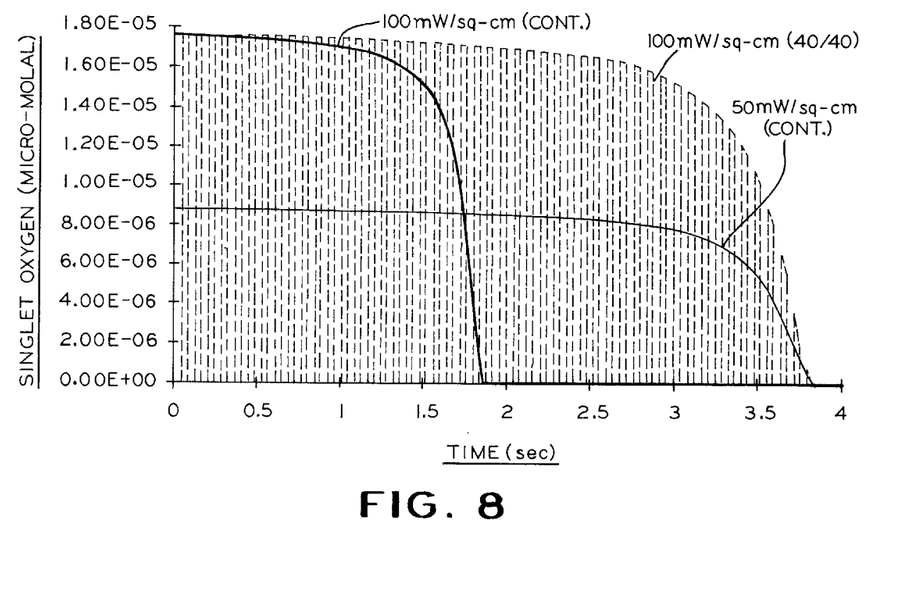
FIG. 8 is a graph comparing a 40 ms fractionation and continuous irradiation.

FIG. 8 shows the transient singlet oxygen concentration in the remote cells for continuous PDT treatment at 50 and 100 $mW/cm^2$ plus a fractionation treatment with a 40/40 ms cycle delivered at 100 $mW/cm^2$. Comparing the continuous 100 $mW/cm^2$ irradiance treatment to the fractionation 100 $mW/cm^2$ treatment, the continuous irradiance depletes oxygen in half the time and is half as effective in treating a sensitized tumor based on the mean doubling time. The fractionation cycle depletes the remote cell singlet oxygen, and reaches its steady state core volume, in the same amount of time as the continuous 50 $mW/cm^2$ irradiance. Such results indicate that oxygen exposure to the tissue outside the SCV is more important than the size of the SVC itself. All cells should be exposed equally to singlet oxygen. The effectiveness of the photodynamic therapy is seriously undermined when cells outside the SCV remain clonagenic.

When too short of a dark interval is used in a fractionation cycle, the oxygen levels in the remote cells are never restored throughout the radiation period. When the singlet oxygen falls to negligible levels in less than 5 seconds, the effectiveness of a two hour treatment is seriously compromised as the remote cells are anoxic and insulated from the direct effects of the PDT. The remote cells may be restoring cell structures which were damaged during the first few seconds of the PDT treatment.

Figure 9:
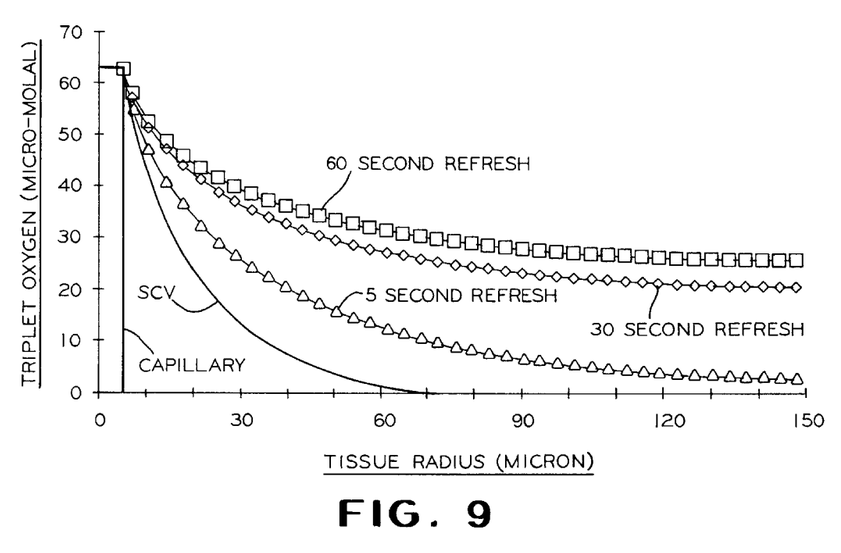
FIG. 9 is a graph showing triplet oxygen refresh profiles and improved oxygen levels upon increase of dark interval as compared to continuous irradiation (SCV)

To overcome hypoxia, longer dark intervals should be utilized, which will allow oxygen to diffuse from the steady state core volume back out to the remote cells. FIG. 9 shows the triplet oxygen refresh profiles for fractionation cycles of 5/5 seconds, 30/30 seconds, and 60/60 seconds. All intervals provide reoxygenation, however higher oxygen levels are achieved as the dark interval is increased.

Figure 10:
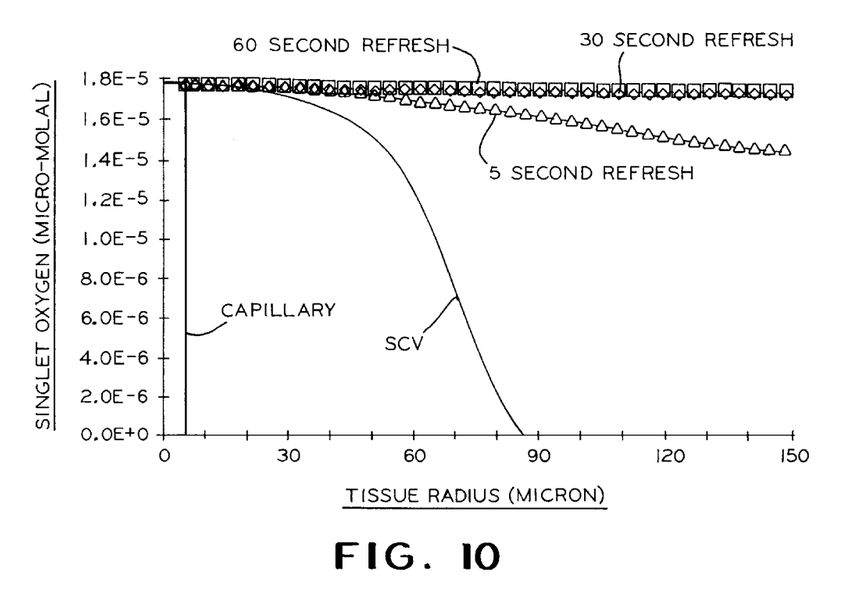
FIG. 10 is a graph showing the singlet oxygen refresh profiles.

Because of the relatively flat relationship between the singlet oxygen and triplet oxygen at high triplet concentrations, there is little difference in the singlet concentrations among the 5, 30, and 60 second recovery times. The singlet oxygen profiles at the end of the light interval are shown in FIG. 10.

The greater the reoxygenation during a dark interval, the more exposure to single oxygen the remote cells will receive on the light interval. With 30/30 second fractionation intervals, the remote cells become anoxic in less than 2 seconds of the initial light interval. Each subsequent light cycle yields only approximately 1.45 seconds of singlet oxygen exposure. For 5/5 second and 60/60 second fractionation interval, the subsequent light intervals yield singlet oxygen exposure times of 0.35 and 1.75 seconds respectively. A 5 second interval provides 720 intervals in a 2 hour treatment for a total singlet oxygen exposure time of only 253.55 seconds. The 30 second interval has 120 intervals with a total exposure time to 174.45 seconds, and the 60 second interval has only 60 intervals with a total exposure time of only 103.25 seconds.

The total singlet oxygen exposure times demonstrate why the fractionation intervals show a marked improvement over continuous irradiation. The exposure times are up to 100 times what the remote cells receive under continuous irradiation.

Estimation of the intercapillary spacing is important in consideration of time fractionation cycles of 5/5 seconds or less. For example, in the R3230AC mammary adenocarcinoma, a 300 $\mu$m spacing results in oxygen barely reaching the remote cells in a 5 second dark interval. In intercapillary spaces of 340 $\mu$m or greater, oxygen would not reach the remote cells at all.

In addition, the fractionation time cycle is not optimal for killing the remote cells. The majority of the light cycle has no effect on the remote cells because the remote cells become anoxic in such a short period of time.

In order to make photodynamic therapy more efficient and a cost-effective treatment for tumors, the fractionation cycle must be optimized and the medical staff must have a convenient means for determining and implementing the PDT treatment. The present invention controls the laser system to achieve the maximum cell destruction in the shortest amount of treatment time.

When the remote cells are unexposed to oxygen, such remote cells remain clonagenic and this degrades the cyotoxic efficiency of the PDT process. As noted above for equal light/dark cycles, the light intervals for all but the shortest intervals is significantly longer than the singlet oxygen exposure times for remote cells.

The fractionation cycle can be improved by maintaining singlet oxygen in the remote cells at a minimum value, increasing the dark cycle and/or reducing the light cycle such that the diffusion and exposure of oxygen is equal, and maximizing the total number of fractionation intervals for a specified treatment time.

Once the oxygen in the remote cells falls below the specified minimum level, the remaining time serves only to deplete oxygen in the tissue between the steady state core volume and the remote cells. In general, the optimum light exposure time should not reduce the remote cell triplet oxygen levels below approximately 1 $\mu$M. Triplet oxygen levels below 1 $\mu$M yield singlet oxygen levels below 50% of the maximum.

The dark intervals also provide opportunities for improvement of the PDT treatment. The initial light interval is terminated at a 1 $\mu$M triplet oxygen level in the remote cells to maintain the minimal oxygen level. The dark interval is maintained until a maximum level of oxygen concentration is achieved. Such a maximum level of oxygen can be set as a percentage of the original oxygen concentration due only to metabolic processes.

Because the oxygen concentration gradient becomes very flat at greater and greater distances from the capillary, a delay in oxygen response is noticed immediately following the light cycle. Since diffusion is driven by the gradient, the oxygen diffuses very slowly at first and is overwhelmed by the metabolic oxygen consumption rate. This results in about a 0.2 second delay in the oxygen response.

Figure 11:
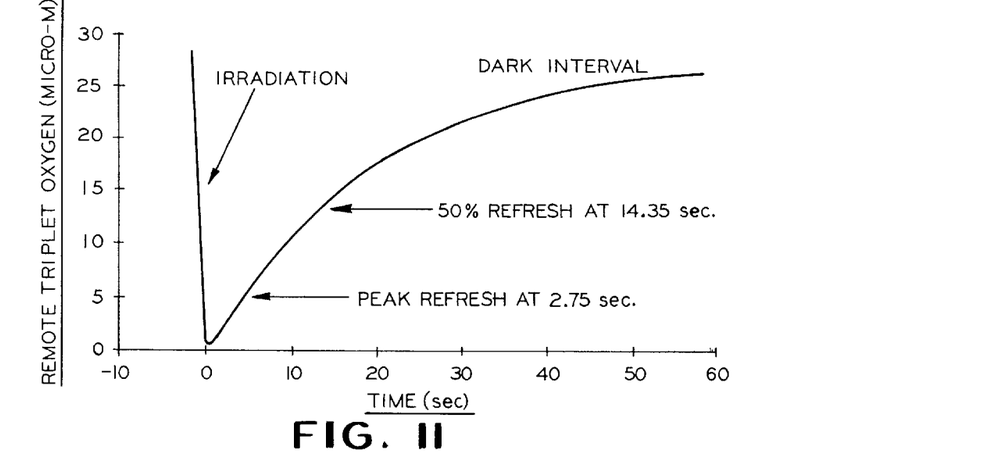
FIG. 11 is a graph showing remote cell triplet oxygen response to dark intervals.

As shown in FIG. 11, the gradient increases as oxygen diffuses outward from the capillary wall. Diffusion of oxygen increases rapidly until a maximum refresh rate is achieved after about 2.75 seconds. The response slows as the oxygen level becomes more uniform between capillaries. In FIG. 11, the oxygen refresh has reached half of the original concentration after approximately 14 seconds.

As time increases, the oxygen levels in the remote cells increases at a much slower rate. The original oxygen level is approached asymptotically and is not reached for several minutes. As the dark interval is lengthened, less and less of an increase in the triplet oxygen concentration is realized.

Since the total cycle time consists of a light interval and a dark interval, the longer dark intervals reduce the number of cycles (and the total exposure time) which can be completed in a fixed length of time. An evaluation must then be made as to the optimum dark interval based on the oxygen levels for each cycle and the number of cycles which can be administered in a specific treatment time.

Figure 12:
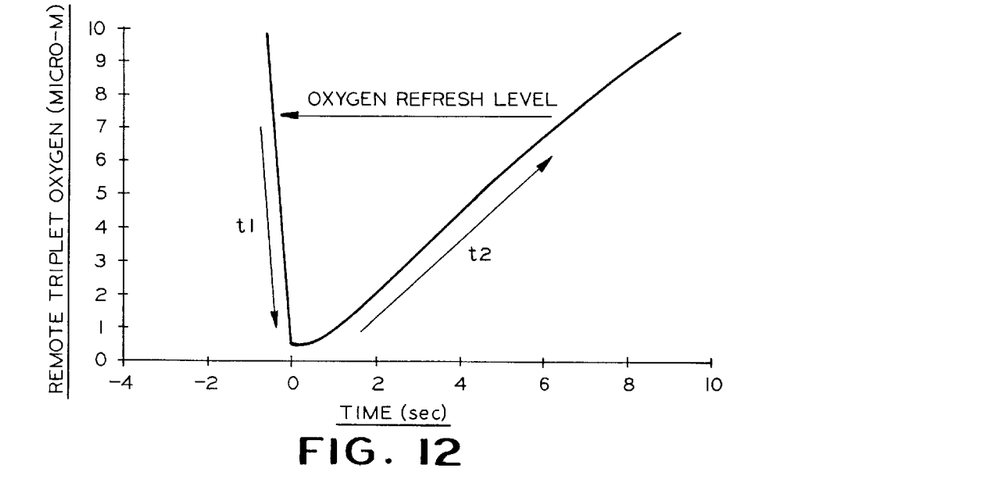
FIG. 12 is a graph showing remote cell triplet oxygen pathway.

FIG. 12 shows the remote cell triplet oxygen response curve. The remote cell oxygen concentration at the end of a dark interval becomes the beginning concentration for the light interval of the next cycle. The light interval time is designated $t_1$ and the dark interval time is designated $t_2$. To optimize the cycle, the ratio of exposure time light interval $t_1$ to the total cycle time $t_1+t_2$ ($\tau$) is maximized.

The light interval portion of the oxygen pathway can be designated as curve fit with a second order polynomial ($f_1$) which describes the time required to deplete the oxygen to 1 $\mu$M as a function of the refresh level C. The dark interval portion of the curve can then be fit with a fourth order polynomial ($f_2$) to describe the time required for reoxygenation to a given refresh level C. Thus, $t_1=f_1(C)$ and $t_2=f_2(C)$ and $F(C)=t_1/(t_1+t_2)$.

Figure 13:
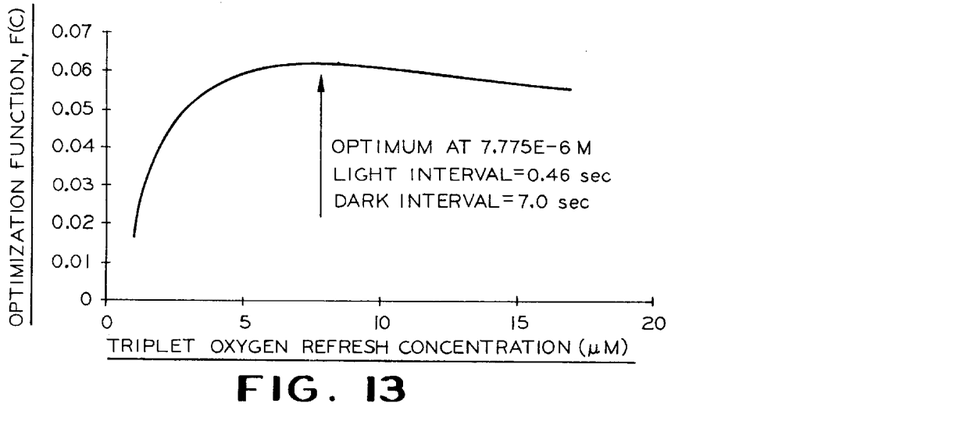
FIG. 13 is a graph showing the time optimization function for maximum remote cell singlet oxygen exposure.

FIG. 13 shows a plot of the optimization function which has a clearly marked optimum refresh concentration. For the function in FIG. 13, the optimum concentration is 7.775 $\mu$M with a light interval of 0.462 seconds and a dark interval of 6.999 seconds for a total cycle time of 7.461 seconds. The peak value of the optimization function is 0.062 indicating that 6.2% of the total cycle time is spent irradiating the entire volume of intercapillary tissue. A 30 second uniform fractionation cycle resulted in only 2.4% of each fractionation cycle being used to irradiate the remote tissue (R3230AC mammary adenocarcinoma).

A two to three fold increase in PDT performance can be achieved by using the optimized light and dark time intervals. The light fractionation system of the present invention allows some tumors to be treated which would otherwise become hypoxic under continuous PDT treatment or under a suboptimum fractionation cycle.

The starting oxygen profile 54 and select output data 56 are used in the system 10 to optimize the fractionation cycle. The output data specifies oxygen as the control variable and allows for data input of the triplet oxygen lower limit and the triplet oxygen upper limit. The computer 30 is programmed to calculate the optimum light and dark intervals.

The initial cycle optimizations will be primarily qualitative at the start. As the simulation results are corrected with the actual treatment results, the results achieved in the simulations will be more accurate. The sensitizer and tumor constants can be considered in a variety of treatment options. Each treatment plan can be stored and recalled by the medical staff when needed for actual treatment of the patient. The computer 30 not only sets the laser parameters, it also controls the beam splitter 26 to achieve an optimum fractionation cycle.

In the treatment process, even small amounts of tissue that are insulated from the direct toxic effect of PDT therapy can have detrimental effects on the success of the PDT process. Controlling the oxygen levels in remote tissue areas through light fractionation provides means to treat certain tumor types that have remained unresponsive to PDT therapy.

Oxygen consumption rates and oxygen diffusion controlled refresh rates are very different. The optimum fractionation cycle should have on-off intervals to optimize the PDT treatment. The optimum intervals for the fractionation cycle are dependent on the irradiance used as well as the spacing of the capillaries within the tumor. In optimizing the fractionation cycle, the number of intervals must also be considered.

The control system 10 of the present invention can also provide a control sequence which provides for a light delivery cycle with an initial fractionated dose of light followed by a continuous dose of light. After an initial period of fractionated light delivery, the integrity of the microvascular system in the tumor and the continued delivery of oxygen to the tumor during fractionated light therapy are at issue.

The computer 30 of the control system 10 may be used to simulate and control the fractionated light therapy as noted above. The initial fractionated cycle treatment is used to kill the remote cells directly. After the initial fractionation therapy, the computer can be used to control a continuous dose of light to the cells within a critical radius. A initial fractionation cycle in a PDT treatment kills the cells outside of the critical radius and a subsequent continuous cycle in the same PDT treatment kills the remaining cells within the critical radius. The computer can simulate both the fractionation cycle and the continuous cycle to create one treatment program combining both type of PDT treatment.

The treatment time for the fractionation cycle and the continuous cycle is determined by the spacing between the capillaries and the percentage of tissue outside and inside of the critical radius. Tumors that are densely populated with capillaries can be treated with almost exclusively with a continuous cycle. Tumors with a high percentage of tissue outside of the critical radius will require more fractionation cycle than continuous cycle during PDT treatment.

The computer 30 of the present invention can simulate the continuous cycle by setting the dark cycle time at zero. The computer 30 processes a simulated treatment with a fractionation cycle and a continuous cycle for control of the laser 22 and the beam splitter 26 during the total treatment. The computer 30 stores in memory the light and dark cycles for the desired time of the fractionation cycle and then the time of the continuous treatment cycle for the balance of the treatment. In general, the light dosage used during the fractionation treatment is less than the light dosage during the continuous treatment.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A system for simulating and controlling a photodynarmic therapy treatment of a sensitized tumor, said system comprising:
    a) a computer system, including a processor for processing input signals and data, simulating a photodynamic therapy treatment of a sensitized tumor to provide a profile of a transient variation of triplet oxygen concentration and determine spatial concentrations of singlet oxygen and photosensitizer as a function of the transient variation of triplet oxygen concentration, determining a fractionation cycle, and generating control signals and output display;
    b) a computer memory included in said computer system and connected to said processor, said memory storing input signals and data, storing results of the simulation and fractionation cycle, and storing the control signals and output displays for subsequent communication with the processor;
    c) input means connected to the processor for transmitting input data regarding triplet oxygen diffusion rates, reaction rate constants, sensitizer parameters, laser operating parameters, starting oxygen parameters, and laser cycle parameters;
    d) output means connected to the processor for displaying the input data and for displaying the selected results of the simulated photodynamic therapy treatment;
    e) a light system for generating a light beam, said light system being connected to the processor for receiving and transmitting light control signals from and to the processor; and
    f) shutter means positioned between said light system and a sensitized tumor for selectively directing the light beam from said light system at the sensitized tumor during a light interval of the fractionation cycle, and then directing the light beam away from the sensitized tumor during a dark interval of the fractionation cycle, said shutter means in electrical communication with said processor for receiving and transmitting shutter control signals from and to the processor, whereby said computer simulates and controls said light system and the fractionation cycle for the photodynamic therapy treatment of the sensitized tumor.

2. The system defined in claim 1, wherein said computer system includes means for setting the light interval and dark interval of the fractionation cycle, and means for converting the light and dark intervals into the shutter control signals to control said shutter means.

3. The system defined in claim 2, wherein the dark interval is longer than the light interval of the fractionation cycle.

4. The system defined in claim 1, wherein said lighting means is a laser system.

5. The system defined in claim 1, wherein said shutter means is a beam splitter.

6. The system defined in claim 1, wherein said computer system includes means for setting the light interval and dark interval of the fractionation cycle, means for setting a subsequent continuous light cycle, and means for converting the light and dark intervals of the fractionation cycle and the continuous light cycle into the shutter control signals to control said shutter means.

7. A method for photodynamic treatment of a sensitized tumor by a computer controlled laser system having a computer with an input means and an output means, said method comprising the steps of:
    a) entering oxygen diffusion rates, reaction rate constants, sensitizer parameters, laser operating parameters, dimensional characteristics and starting oxygen profile parameters into the computer;
    b) selecting a lower limit and an upper limit for triplet oxygen concentration in the tumor and entering the limits into the computer;
    c) selecting output data to be observed at the output means;
    d) computing an optimum fractionation cycle of the photodynamic therapy treatment, including a light interval and dark interval for the fractionation cycle;
    e) simulating the photodynamic treatment of the tumor in the computer to provide a profile of a transient variation of triplet oxygen concentration and determine spatial concentrations of singlet oxygen and photosensitizer as a function of the transient variation of triplet oxygen concentration and observing the output data;

f) storing in computer memory the data entered into the computer and output data of the simulated treatment; and g) conducting an actual photodynamic treatment of a tumor by recalling the data from the memory and transmitting control signals from the computer to the laser system to control the fractionation of the laser beam directed at the tumor.

8. The method defined in claim 7, including an additional step, after conducting an actual photodynamic treatment, of correlating the actual results from the treatment with the projected results from the computer simulation of the treatment.

9. The method defined in claim 7, including additional steps, after simulating the photodynamic treatment of the tumor, of adjusting data entered into the computer;

conducting an additional simulation and storing the data from the additional simulation;

repeating the data adjustment, treatment simulation, and data storage steps until a plurality of treatments have been simulated; and, prior to conducting an actual treatment, selecting a desired treatment from the computer memory for conducting the actual photodynamic treatment.

10. The method defined in claim 7, wherein the simulating of the treatment and the conducting of the actual treatment include transmitting and receiving laser control signals from the computer to a laser to control the laser operating parameters, and transmitting and receiving shutter control signals from a shutter means to control the fractionation cycle for the photodynamic treatment.

11. A method for photodynamic treatment of a sensitized tumor by a computer controlled laser system having a computer with an input means and an output means, said method comprising the steps of:

a) entering oxygen diffusion rates, reaction rate constants, sensitizer parameters, laser operating parameters, dimensional characteristics and starting oxygen profile parameters into the computer;

b) selecting a lower limit and an upper limit for triplet oxygen concentration in the tumor and entering the limits into the computer;

c) selecting output data to be observed at the output means;

d) computing an optimum fractionation cycle and a continuous cycle for the photodynamic therapy treatment, including the light interval and dark interval for the fractionation cycle;

e) simulating the photodynamic treatment of the tumor in the computer to provide a profile of a transient variation of triplet oxygen concentration and determine spatial concentrations of singlet oxygen and photosensitizer as a function of the transient variation of triplet oxygen concentration and observing the output data;

f) storing in computer memory the data entered into the computer and output data of the simulated treatment;

g) conducting an actual photodynamic treatment of a tumor by recalling the data from the memory and transmitting control signals from the computer to the laser system to control the initial fractionation of the laser beam and the subsequent continuous laser beam direct at the tumor.

12. A method for photodynamic therapy treatment of a tumor infused with a photosensitizer by a computer controlled laser, the method comprising the steps of:

a) simulating a photodynamic therapy treatment of the tumor to provide a profile of a transient variation of triplet oxygen concentration;

b) determining spatial concentrations of singlet oxygen and photosensitizer as a function of the transient variation of triplet oxygen concentration; and c) adjusting a fractionation cycle of the computer controlled laser as a function of the transient variation of triplet oxygen concentration and spatial concentrations of singlet oxygen and photosensitizer to provide a desired singlet oxygen concentration level in the tumor.

13. The method of claim 12 wherein the spatial concentration of triplet photosensitizer and singlet photosensitizer are determined.

* * * * *